(12) United States Patent
Mollus et al.

(10) Patent No.: US 7,203,534 B2
(45) Date of Patent: Apr. 10, 2007

(54) METHOD OF ASSISTING ORIENTATION IN A VASCULAR SYSTEM

(75) Inventors: Sabine Mollus, Kall (DE); Kai Eck, Aachen (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 578 days.

(21) Appl. No.: 10/323,145

(22) Filed: Dec. 18, 2002

(65) Prior Publication Data

US 2003/0123606 A1 Jul. 3, 2003

(30) Foreign Application Priority Data

Dec. 19, 2001 (DE) ................................ 101 62 272

(51) Int. Cl.
*A61B 5/05* (2006.01)

(52) U.S. Cl. ..................... 600/425; 600/431; 600/433; 600/454; 600/481; 324/309; 348/45; 348/77

(58) Field of Classification Search ................ 600/425, 600/431, 433, 481; 324/309; 348/45, 77
See application file for complete search history.

(56) References Cited

U.S. PATENT DOCUMENTS

| 5,274,551 A | * | 12/1993 | Corby, Jr. .................... 600/433 |
| 5,458,126 A | * | 10/1995 | Cline et al. ................. 600/425 |
| 6,031,362 A | | 2/2000 | Bradley |
| 6,428,482 B1 | * | 8/2002 | Sunagawa et al. .......... 600/485 |
| 2002/0137014 A1 | * | 9/2002 | Anderson et al. ........... 434/262 |

FOREIGN PATENT DOCUMENTS

| DE | 10047314 A1 | 4/2001 |
| WO | WO 00/39753 | 7/2000 |

* cited by examiner

*Primary Examiner*—Brian L. Casler
*Assistant Examiner*—Baisakhi Roy

(57) ABSTRACT

The invention relates to a method of forming a very accurate vascular map or road map to be associated with the current X-ray image during an invasive vascular intervention. The vascular map is derived from a four-dimensional model of the vascular tree, that is, from a spatially three-dimensional, time-dependent model, the time dependency relating to natural motions of the body such as notably the heartbeat and/or the respiration. In particular the rhythm of the heartbeat or the respiration can be determined by means of a sensor so as to be used for synchronized selection and display of the corresponding three-dimensional vascular model.

16 Claims, 1 Drawing Sheet

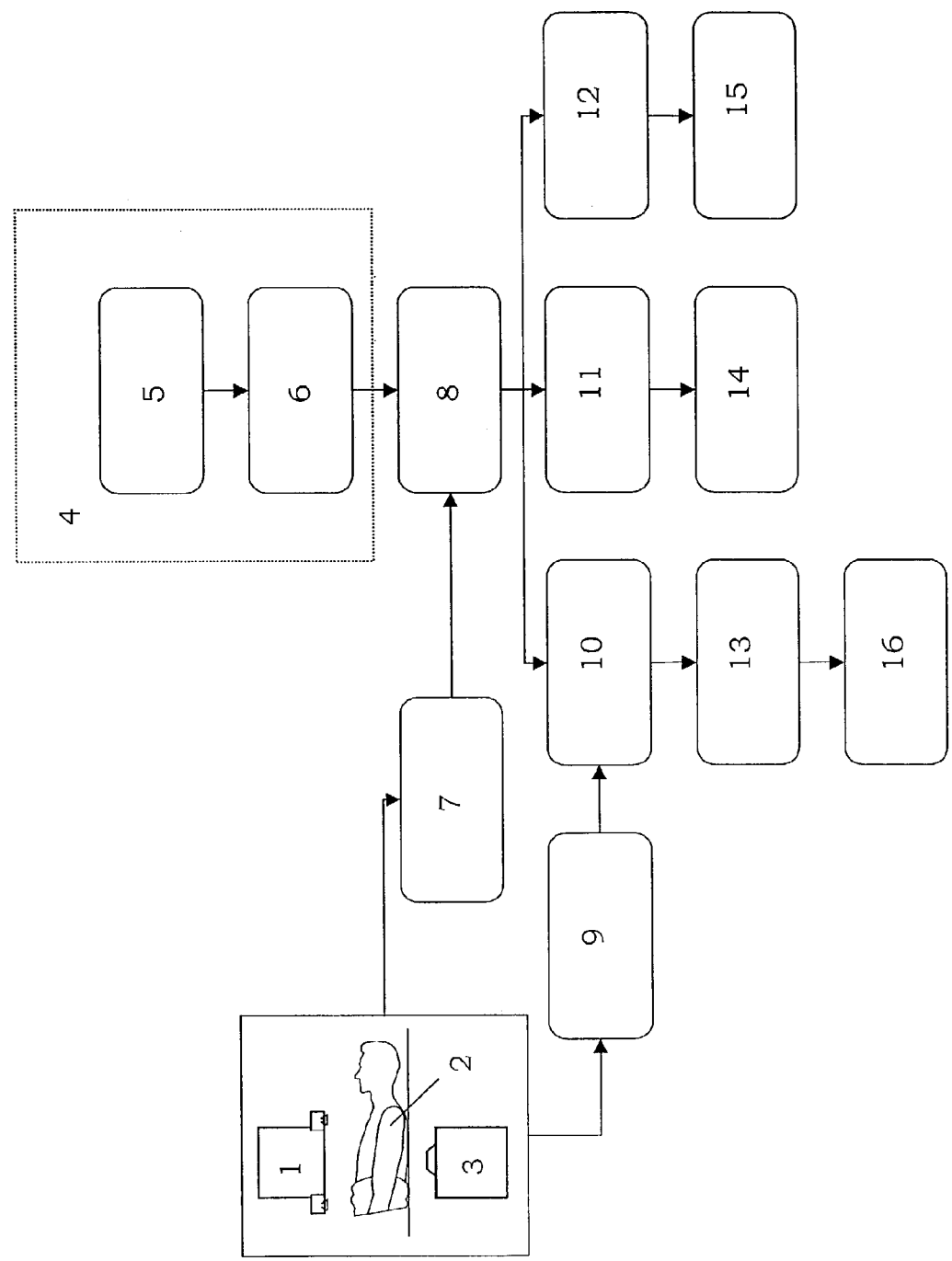

METHOD OF ASSISTING ORIENTATION IN A VASCULAR SYSTEM

BACKGROUND

The invention relates to a method of assisting orientation in the vascular system of a body volume. The invention also relates to an X-ray apparatus for monitoring an invasive vascular operation.

DE 100 47 314 A1 discloses a method of assisting orientation during angioscopy; this method utilizes a three-dimensional model of the vascular tree of the blood vessels. Using an X-ray fluoroscope, the position of a catheter or a guide wire is tracked in a two-dimensional projection during the angioscopic intervention while the physician has the possibility of changing the projection direction at will. Each time the instantaneous projection direction is detected and the corresponding projection of the three-dimensional model of the vascular tree is calculated. The latter can then be superposed on the instantaneous X-ray fluoroscopic image, it notably being possible to highlight the course of the vessels in the region of the tip of the catheter, as determined from the model, in the fluoroscopic live image in a "virtual contrast medium injection". This method has a drawback, however, in that there is often inadequate spatial correspondence between the X-ray fluoroscopic live image and the projection of the model, that is, in particular in the case of small vessels.

SUMMARY OF THE INVENTION

Considering the foregoing it is an object of the present invention to provide an improved method and an improved X-ray apparatus which offer a higher precision when combining a fluoroscopic with a vascular model.

This object is achieved by means of a method as disclosed in claim 1 as well as by means of an X-ray apparatus as disclosed in claim 9. Advantageous further embodiments are disclosed in the dependent claims.

The method in accordance with the invention is intended to assist orientation in the vascular system of a body volume. It can be advantageously used notably in the case of invasive vascular operations which may serve diagnostic as well as therapeutic purposes and are usually performed by means of a catheter or a guide wire. The method includes the following steps:
a) acquisition of models of the vascular system in the relevant body volume in different phases of a natural motion of the body. In this context a "model" is to be understood to mean any quantity of data that is suitable for a geometrical description of the vascular system; this may notably concern a binary or vectorial representation of the vascular tree. Preferably, the models are three-dimensional so that they represent the spatial shape of the vascular tree. The natural motion of the body may notably be a cyclical natural motion such as the heartbeat and/or the respiration.
b) forming a graphic representation on the basis of at least one of the models of the vascular system and a current image of the body volume. The image may notably be a fluoroscopic image, such as an X-ray image, which will often be referred to and observed by way of example hereinafter. However, the method is in principle not restricted thereto and may also be used, for example, in conjunction with magnetic resonance (MR) methods, sonographic methods, scintigraphic methods or the like.

According to the method in accordance with the invention natural motions of the body, such as notably the heartbeat and/or the respiration, which have a significant effect on the shape and position of the vessels are taken into account. For example, the heartbeat changes the shape of the heart and its vessels and indirectly also the position of vessels in neighboring organs. The same holds for the lung or the thorax during respiration. In accordance with the invention such natural motions of the body are taken into account in that different models of the vascular system are acquired and used for different phases of these natural motions. This enables exact orientation in the body volume observed, so that not in the least the patient burden in the form of contrast medium and X-ray dose can be reduced.

In conformity with a further version of the method the instantaneous natural motion of the body is determined via suitable sensors and in step b) of the method the model of the vascular system which best fits the current phase of the natural motion is used. It is thus automatically ensured that the model used is synchronized with the natural motion of the body. In step b) it is notably possible to display the model (two-dimensional or three-dimensional) which best fits the instantaneous phase of the natural motion of the body on a monitor in synchronized form while the current image is preferably displayed in parallel on a second monitor.

Preferably, a two-dimensional projection of a three-dimensional model of the vascular system is used in step b). In respect of the type of image, such a two-dimensional projection corresponds to a normal two-dimensional fluoroscopic image, so that the physician can suitably compare the two images.

According to the above procedure, in the simplest case the direction and/or plane of the two-dimensional projection of a three-dimensional model can be selected by the physician on the basis of considerations of effectiveness. Preferably, however, the projection direction and/or projection plane of the three-dimensional models are especially selected in such a manner that they correspond to the projection direction and/or projection plane of the current fluoroscopic image. In the case of parallel display of the model projection and the current fluoroscopic image, the projections then correspond so that direct comparison is possible.

The projection direction and/or the projection plane of the current fluoroscopic image can be derived from data provided by the acquisition apparatus. Because of mechanical tolerances, however, the accuracy of this data generally is limited, so that typically an angular error of approximately ±2° occurs. Better correspondence can be achieved between the projection directions and/or projection planes of the current fluoroscopic image and the model in accordance with the invention by comparing the current fluoroscopic image with (fluoroscopic) images of the relevant body volume which have been formed and used so as to form the models of the vascular system. This is because in forming the models of the vascular system the body volume of interest is generally imaged from various directions (preferably from all directions during a rotary movement) and subsequently the (three-dimensional) vascular system is reconstructed from the numerous two-dimensional projections thus obtained. In accordance with the proposed method from among the two-dimensional projections obtained those two-dimensional projections whose projection directions and/or projection planes are situated near the provisionally determined projection direction and/or projection plane of the current fluoroscopic image are compared with the current fluoroscopic image. That one of these projections which exhibits the best correspondence with the current fluoroscopic image is then considered as an image from the same direction or with the same projection image as the live image, and the parameters on which this projection is based are used for the selection of the projection direction and/or projection plane of the model.

In accordance with a further version of the method the position of an object, such as notably an instrument, a catheter or a guide wire, is determined from the current image and the corresponding position is highlighted in the models of the vascular system. The physician can thus recognize immediately where the relevant object is currently situated in the rendition of a model of the vascular system.

A further possibility for forming a graphic representation in the step b) of the method consists in that at least one model of the vascular system is superposed on the current image. The combined representation in a single image enables the model data to be related directly to the current image data.

The invention also relates to an X-ray apparatus for monitoring an invasive vascular operation, which apparatus includes the following elements:
- an X-ray source and a detector for forming X-ray images of a predetermined body volume. These components are preferably associated with one another so as to be rotatable with a fixed relative geometry. The X-ray source and the detector are typically attached to the ends of a so-called C-arm which is rotatable about its center. The acquisition device can thus be moved along a circular path around the body of a patient, so that from different viewing directions images can be formed of a body volume of interest which is situated at the center of the rotary motion.
- a memory for storing models of the vascular system of said body volume in different phases of a natural motion of the body. The models may have been acquired in advance during a separate examination at a substantial distance in time from the current examination or may also be acquired during the current examination. They may have been acquired by means of the same X-ray apparatus or also by means of other apparatus such as an X-ray computed tomography (CT) apparatus or an MR apparatus. Furthermore, they may be two-dimensional or three-dimensional.
- a sensor for the natural motion of the body. The natural motion of the body may notably be a patient's heartbeat and/or respiration. The sensor may in that case be an ECG apparatus or an apparatus which is suitable for monitoring the respiration.
- a data processing unit which is coupled to said sensor and to said memory and is arranged in such a manner that it forms a graphic representation on the basis of at least one of said models and on a current X-ray image of the body volume.

The described X-ray apparatus enables very precise monitoring of an invasive vascular operation, because it has a time-dependent model of the vascular system available in its memory and utilizes it for combination with the current live image of the body. The instantaneous state of the natural motion of the body can be tracked via the sensor of the device, so that the relevant compatible model can be selected and used in synchronism for the formation of the graphic representation.

A further embodiment of the X-ray apparatus in accordance with the invention includes a device for determining the current image plane or projection direction of the X-ray image. Such a device is capable, for example, of measuring the angular position of the X-ray source and/or the detector and to forward the data thus acquired to the data processing unit so that it can be taken up in the formation of the common representation.

The following description, claims and accompanying drawing sets forth a certain illustrative embodiment(s) applying various principles of the present invention. It is to be appreciated that different embodiments applying principles of the invention may take form in various components, steps and arrangements of components and steps. The described embodiment(s) being indicative of but one or a few of the various ways in which some or all of the principles of the invention may be employed in a method or apparatus. The drawing is only for the purpose of illustrating an embodiment of an apparatus and method applying principles of the present invention and is not to be construed as limiting the present invention.

DESCRIPTION OF THE DRAWING

The invention will be described in detail hereinafter with reference to the FIGURE. The sole FIGURE is a diagrammatic representation of the components of an X-ray apparatus in accordance with the invention.

DESCRIPTION

The imaging section of an X-ray apparatus, consisting of an X-ray source 3 and an X-ray detector 1, is diagrammatically shown at the left-hand side of the FIGURE, said components typically being mounted on a rotatable C-arm. Between said elements there is arranged a patient 2 so that a body volume of interest of the patient can be imaged by X-ray fluoroscopy. The present case concerns in particular the monitoring of an invasive diagnostic or therapeutic intervention in the vascular system of the patient. A catheter (possibly with a guide wire) is then advanced through the vessels as far as or into the body volume to be treated. The navigation of this catheter is supported in a usual manner by serial X-ray images showing the physician the current position of the catheter. In practice the so-called fluoroscopic mode of low X-ray dose as well as the so-called cine mode of higher X-ray dose can be distinguished in such a case. During the cine mode contrast medium is generally injected into the vascular system via the catheter, so that the topology of the vascular tree is visible for a sequence of from four to five cardiac cycles.

Fluoroscopy is usually carried out so as to reach a constriction of the vascular system by means of the guide wire without using a contrast medium and to position the instrument on the guide wire, moved beyond the constriction, on the constriction. The correct position is verified, after the positioning, by means of a small surge of contrast medium in the fluoroscopic mode and is possibly corrected in a complex iterative process requiring a large amount of time and a large dose. If no contrast medium is applied in the fluoroscopic mode, the image sequences in this mode show only the catheter, the guide wire and the instruments as well as some background information. Because of the small differences in absorption density in comparison with the surrounding tissue, it is practically impossible to recognize the vessels themselves.

The physician can change the viewing angle and the position of the imaging system during the intervention in order to view the vascular tree in which the instruments are currently present from different perspectives. In order to assist the physician in navigating through the vascular system, the state of the art utilizes only static images (vascular maps or road maps) selected from a plurality of previous images formed in the cine mode. Static images of this kind, however, do not take into account a natural motion of the body which is caused notably by the heartbeat and/or the respiration of the patient 2.

In order to improve this situation, the invention proposes the use of time-dependent, spatially three-dimensional vascular models which may also be referred to as "four-dimensional" vascular models when time is defined as the fourth dimension. These models are acquired either in a separate process 4 (long) before the actual intervention, or can also be formed during the intervention itself. The models can be generated notably by means of so-called "rotating angiography" during which the X-ray source 3 and the detector 1 rotate around the patient while generating images from different directions. Block 5 in the FIGURE represents the memory for the models.

In a further preprocessing step, symbolized by the block 6, various projections of the models from the block 5 are calculated in preparation. These are projections which are defined by two angular values in conformity with the geometrical viewing direction as well as by two phase angles (measured between 0 and $2\pi$) of the cardiac cycle and the respiratory cycle. Because of the large amount of calculation work required for generating these projections, they are preferably calculated in advance and not in real time. However, calculation in real time is possible when an appropriate calculation capacity is available and/or when the amount of work is reduced, for example, by utilizing a lower resolution level.

During the actual examination, the processing steps 7 to 16 are carried out. First the physician forms X-ray fluoroscopic image sequences (block 9). In order to enable viewing of the different perspectives of the vascular tree, the physician changes the angle and the position of the imaging system 1, 3 as necessary. The instantaneous position data of the system is continuously determined by means of a position detection system 7.

In the block 8 that projection whose parameters correspond best to the instantaneous data presented by the position detection system 7 can be selected from among the pre-calculated projections 6. Because the imaging system 1, 3 has six degrees of freedom in respect of positioning, the projection of the vascular system or road map selected in the block 8 may also be referred to as a "6F road map".

There are various possibilities for the correlation and combination of the current fluoroscopic image sequence 9 and the 6F road maps determined from the three-dimensional vascular models; three of these possibilities are shown in the FIGURE.

In the simplest case the user selects a preferred one of the presented 6F roadmaps or vascular maps in the block 11. This is typically a map that is associated with a specific phase of the cardiac cycle or respiratory cycle. This vascular map is then displayed on a second monitor which is arranged above the monitor which displays the fluoroscopic live image (block 14).

In conformity with a second version which is shown in the blocks 12 and 15, the ECG and the respiration of the patient are determined by means of additional sensors (not shown) and an associated vascular map is automatically selected from the block 8 in dependence on the current phases of the heartbeat and the respiration thus determined. The vascular map which is synchronous with this current state of the body is then displayed (in the block 15) on a second monitor in parallel with the fluoroscopic live image.

Finally, the blocks 10, 13 and 16 illustrate a further possibility for display where indicators for the instruments are statically or dynamically integrated in more complex methods. In the block 10 first registration is performed between the fluoroscopic live image and the three-dimensional vascular model or its two-dimensional projection (vascular map); this means that corresponding points are searched in the two images. In the block 13 an extraction of the instrument, such as, for example, the catheter tip, is performed. Algorithms which are suitable in this respect are described, for example, in WO 00/39753. In the block 16 indicators for the instrument can be statically or dynamically inserted in the fluoroscopic image and/or in a rendition of the vascular model. Furthermore, after the registration in the block 10, digital subtraction angiography (DSA) may also be carried out; during such subtraction angiography the difference is formed between the current image and a reference image in order to attenuate non-interesting structures and to enhance structures of interest.

Having described a preferred embodiment of the invention, the following is claimed:

1. A method of assisting the orientation in the vascular system of a body volume, the method comprising:
    (a) acquisition of three-dimensional models of the vascular system in the body volume in different phases of a natural motion of the body based on changes due to one or more internal biological functions;
    (b) sensing a current phase of natural motion of the body;
    (c) selecting one of the three-dimensional models of the vascular system that best fits the current phase of natural motion;
    (d) forming a graphic representation on the basis of the selected three-dimensional model and a current image of the body volume; and
    (e) repeating the selecting step and forming step for each of the current images.

2. The method of claim 1 wherein a two-dimensional projection of a three-dimensional model is formed in the step d).

3. The method of claim 2 wherein the current image is a fluoroscopic image and at least one of the projection direction and the projection plane of the three-dimensional model corresponds to at least one of the projection direction and the projection plane of the fluoroscopic image.

4. The method of claim 3 wherein at least one of the projection direction and the projection plane of the current fluoroscopic image is determined by comparing the fluoroscopic image with images of the body volume which were used for deriving the three-dimensional models of the vascular system.

5. The method of claim 1 wherein the position of an object within an imaging region is determined from the current fluoroscopic image and that the corresponding position is highlighted in the rendition of the models of the vascular system.

6. The method of claim 5 wherein the object within the imaging region comprises at least one of an instrument, a catheter and a guide wire.

7. The method of claim 1 wherein the natural motion of the body is caused by at least one of heartbeat and respiration.

8. An X-ray apparatus for monitoring an invasive vascular operation comprising:
    an X-ray source and a detector for forming X-ray images of a predetermined body volume;

a memory for storing models of the vascular system in the body volume in different phases of a natural motion of the body based on changes due to one or more internal biological functions;

a sensor for a current phase of natural motion of the body;

means for selecting the model of the vascular system which best fits the current phase of the natural motion;

means for updating the selection of the model as the current phase of natural motion changes; and a data processing unit which is coupled to the sensor and to the memory and is arranged in such a manner that it forms a graphic representation on the basis of the selected model of the vascular system and the current X-ray image of the body volume.

9. The X-ray apparatus of claim 8 comprising a device for determining at least one of a current projection direction and projection plane of the X-ray image.

10. The apparatus of claim 8, wherein the internal biological function at least one of respiration or cardiac activity.

11. An apparatus for assisting the orientation in the vascular system of a body volume, the apparatus comprising:

means for acquisition of three-dimensional models of the vascular system in the body volume in different phases of a natural motion of the body based on changes due to internal biological functions;

means for sensing a current phase on natural motion of the body;

means for selecting the three-dimensional model that best fits the current phase of natural motion;

means for updating the selection of the three-dimensional model as the current phase of natural motion changes; and means for forming a graphic representation on the basis of the selected three-dimensional model and a current image of the body volume.

12. The apparatus of claim 11 comprising means for forming a two-dimensional projection of a three-dimensional model.

13. The apparatus of claim 12 comprising a fluoroscope for providing the current image and means for corresponding at least one of the projection direction and the projection plane of the three-dimensional model to at least one of the projection direction and the projection plane of the current fluoroscopic image.

14. The apparatus of claim 11 comprising means for determining the position of an object within an imaging region and means for highlighting the corresponding position in the rendition of the models of the vascular system.

15. The apparatus of claim 14 wherein the means for determining the position of the object within an imaging region includes a fluoroscopic image.

16. The apparatus of claim 11 comprising means for superposing the selected three-dimensional model of the vascular system on a rendition of the image.

* * * * *